United States Patent
Denner et al.

(10) Patent No.: US 10,088,441 B2
(45) Date of Patent: Oct. 2, 2018

(54) METHOD AND DEVICE FOR MATERIAL ANALYSIS

(71) Applicant: Netzsch-Gerätebau GmbH, Selb (DE)

(72) Inventors: Thomas Denner, Selb (DE); Juergen Blumm, Selb (DE); Otto Max Schaefer, Selb (DE); Markus Hollering, Wunsiedel (DE); Matthias Gradl, Sesslach (DE); Gunther Herr, Haarth (DE); Andre Nijmeh, Merkendorf (DE); Thilo Hilpert, Selb (DE); Alexander Frenzl, Schoenwald (DE); Stefan Lauterbach, Selb (DE); Andreas Strobel, Auerbach (DE); Gabriele Kaiser, Selb (DE); Stefan Schmoelzer, Issigau (DE); Markus Meyer, Ehingen (DE); Stephan Knappe, Doehlau (DE); Rolf Preuss, Einbeck (DE); Michael Gebhardt, Selb (DE); Elena Moukhina, Selb (DE); Alexander Schindler, Leupoldsgruen (DE)

(73) Assignee: Netzsch-Gerätebau GmbH, Selb (DE)

( * ) Notice: Subject to any disclaimer, the term of this patent is extended or adjusted under 35 U.S.C. 154(b) by 490 days.

(21) Appl. No.: 14/839,160

(22) Filed: Aug. 28, 2015

(65) Prior Publication Data
US 2015/0369765 A1 Dec. 24, 2015

Related U.S. Application Data

(63) Continuation of application No. PCT/DE2014/000105, filed on Mar. 4, 2014.

(30) Foreign Application Priority Data

Mar. 4, 2013 (DE) .......... 10 2013 102 088

(51) Int. Cl.
*G01K 17/00* (2006.01)
*G01N 25/00* (2006.01)
(Continued)

(52) U.S. Cl.
CPC ............ *G01N 25/20* (2013.01); *G01K 17/00* (2013.01); *G01N 25/4893* (2013.01); *Y10T 29/49828* (2015.01)

(58) Field of Classification Search
USPC ............... 374/31, 10, 12, 14, 11, 13, 208
See application file for complete search history.

(56) References Cited

U.S. PATENT DOCUMENTS 3,491,581 A   1/1970 Roberts et al.
4,056,407 A * 11/1977 Cure .................. G01K 7/02
                                                136/232
(Continued)

FOREIGN PATENT DOCUMENTS

DE   1178235 B   9/1964
DE   3004810 A1  8/1981
(Continued)

OTHER PUBLICATIONS

International Search Report Application No. PCT/DE2014/000105 Completed: Aug. 7, 2014; dated Aug. 26, 2014 5 pages.

*Primary Examiner* — Mirellys Jagan
(74) *Attorney, Agent, or Firm* — Whitmyer IP Group LLC

(57) ABSTRACT

Method and thermal analysis device including a sample holder and at least one temperature detector which is assigned to the holder. The invention further relates to a production method for a temperature detector. A heat flow to be detected is conveyed to the temperature detector between a support surface and the sample holder, wherein the support surface and/or the sample holder include elevations or depressions forming contact points, which define a relevant heat flow zone assigned to the support surface. A thermocouple, which includes at least two elements made of different metals, a first metallic element A, with a higher (Continued)

expansion coefficient compared to a second metallic element B, is introduced in a precisely fitting manner into second metallic element B constituted as a hollow profile and the two elements A, B are heated in a first operational step and then cooled again in a second operational step.

16 Claims, 3 Drawing Sheets

(51) Int. Cl.
      *G01K 1/00*         (2006.01)
      *G01N 25/20*      (2006.01)
      *G01N 25/48*      (2006.01)

(56) References Cited

U.S. PATENT DOCUMENTS

| | | | | |
|---|---|---|---|---|
| 4,059,996 A | * | 11/1977 | Cure | B01L 3/04 |
| | | | | 136/230 |
| 5,321,719 A | | 6/1994 | Reed et al. | |
| 7,588,366 B2 | * | 9/2009 | Kinoshita | G01N 25/4866 |
| | | | | 374/112 |
| 8,042,992 B2 | * | 10/2011 | Wijffels | G01N 25/482 |
| | | | | 374/12 |

FOREIGN PATENT DOCUMENTS

| | | |
|---|---|---|
| DE | 201516 A1 | 7/1983 |
| EP | 1528392 A1 | 5/2005 |
| FR | 2929012 A1 | 9/2009 |

\* cited by examiner

METHOD AND DEVICE FOR MATERIAL ANALYSIS

FIELD OF THE INVENTION

The invention relates to a method and a thermal analysis device comprising a holding device with a support surface for a sample holder and at least one temperature detection means, which is assigned to the sample holder. Furthermore, the invention relates to a sample holder and a production method for a temperature detector for a thermal analysis device.

BACKGROUND OF THE INVENTION

A thermal method for material analysis is for example differential thermal analysis (DTA) from the group of methods for thermal analysis. DTA is based on a characteristic energy conversion during the phase transition and enables the qualitative analysis. Temperatures of the sample and of a selected reference substance are each measured and compared in a crucible in a symmetrical measurement chamber. The reference substance is selected such that it does not exhibit any phase transitions in the temperature range to be investigated. A constant energy supply takes place by means of a furnace. The temperatures beneath both crucibles are measured by a temperature sensor and the occurring difference is recorded. Only with phase transitions does such a temperature difference occur, from the curve shape whereof conclusions can then be drawn as to the composition of the sample. Frequent areas of application of DTA are the investigation of mineral substances, such as for example clinker phase formation in cement raw meal, the detection of the heat of reaction in the combustion of organic substances and the characterisation of plastics.

Dynamic differential calorimetry (engl. differential scanning calorimetry, DSC) has been developed further from DTA. Instead of directly recording the temperature difference between the two crucibles as a function of the supplied energy and the temperature of the reference substance as in the case of DTA, the heat flow difference is determined therefrom in the case of DSC. Dynamic differential calorimeters (DDK, engl. dynamic differential scanning calorimeters, DDSC) are used for the analysis of polymers, pharmaceutical materials, textiles, metals, ceramics and other organic and inorganic materials. Various material properties such as phase transition temperatures, specific heats, melting and solidification temperatures, etc. can be derived from the measured magnitudes. The method of dynamic differential calorimetry is established and standardised worldwide (ISO 11357, DIN 52765, ASTM E 967, ASTM 968 or ASTM D 3418). A distinction is made between power-compensating DSC and heat flow DSC.

In the case of these measuring devices, two ceramic or metallic crucibles are typically used to receive a sample and a reference. In the case of a power-compensating DSC, the two crucibles are inserted separately into two small furnaces, which are often equipped with resistance heating such as for example a platinum heating coil. Apart from this, there are various possibilities for cooling such as for example liquid nitrogen cooling, compressed air cooling, mechanical cooling systems and so forth. Both crucibles are subjected to the same temperature program. The difference in the electrical power that is required to keep a temperature difference between the two crucibles constant, typically at zero, is measured. PT100 resistance thermometers, welded thermocouples or thermopiles are usually used nowadays in practice as temperature measuring devices.

With heat flow DSCs, on the other hand, there is only one furnace, which is usually heated with the aid of resistance heaters such as for example jacket heating conductors. For the cooling, the same methods are available as for power-compensating. A sensor with two support surfaces or defined positions for the sample and the reference is installed in the furnace. The support surfaces can for example be integrated into a disc or be located on a cylindrical elevation. They are contacted with temperature measuring devices (PT100 resistance thermometers, thermocouples or thermopiles) and are each provided with a corresponding crucible during the measurements. The heat flow difference or the temperature difference between the two positions is measured directly using the temperature measuring devices.

The temperature difference can be converted into a heat flow difference if the DSC device has undergone a calibration. This can take place with reference materials, the relevant thermal properties whereof (e.g. temperature onset and enthalpy of phase transitions, specific heat capacity as a function of the temperature) are precisely known. A very important reference material of DSC is indium.

The accuracy of the measurement of the heat flow depends on how well the measurement signal can be reproduced when the actual heat flow of a sample is the same. An essential pre-requisite for good reproducibility is that the overall thermal resistance along the heat flow path between the sample and the reference remains as far as possible identical in successive measurements. The overall thermal resistance results from the sum of the individual resistances along the heat flow path. The latter are determined essentially by the thermal conductivities of the materials used, the geometry of the components and the contact resistances at interfaces (e.g. crucible/sensor).

Heat flows which take place by heat conduction through the surrounding gas, convection and radiation must not however be overlooked. With regard to the heat conduction through the surrounding gas, this can be detected in the case of heat flow DSC by measurements of the melting process of indium in different gas atmospheres. If the melting of indium is measured once under helium and then the same sample under the same measurement conditions under argon, the integral of the melting peak in the temperature difference curve for the measurement under argon is greater than under helium. The reason for this is the markedly lower thermal conductivity of argon compared to helium. In the case of the measurement under helium, therefore, a greater part of the heat flow between the indium sample and the reference flows via the gas than under argon. This proportion of the heat flow, however, is virtually undetected by the temperature measuring devices and the temperature difference measured by the temperature measuring devices thus produces a smaller integral in the case of helium. In practice, this phenomenon is taken into account by calibrations depending on the type of gas.

Crucibles of different shape made of different materials are used for the measurements depending on the application and its particular requirements. The mass of the crucibles should be as small as possible, the heat conduction should be good and, for industrial use, the price should be as low as possible. A frequently used material, therefore, is aluminium. The wall and base thicknesses of the crucibles lie in the range of a few tenths of a millimeter, the filling volume between a few tens and a few hundred microliters. In order that the thermal resistance is maintained and therefore the accuracy of the heat flow measurement is not impaired, the actual contact surfaces between the crucible base and the support surface must not vary for different crucibles. The problem here, in particular, is that the crucible bases can deviate from an ideally flat shape in an uncontrolled and non-reproducible manner on account of the small material thickness. This may be caused by production, but also by deformation during handling. A curvature of the crucible base outwards becomes evident in a particularly disadvantageous manner.

The individual components of the sensor, i.e. in particular the support surfaces and temperature measuring devices, are fixedly connected to one another, so that the resistance for the heat flow in this region does not change or changes only negligibly over a large number of measurements. Measurable changes can be compensated for by a recalibration. On the other hand, the thermal contact between the sample and the crucible and between the crucible and the sensor are more critical, because easy separability is usually desired at these points for practical reasons of handling.

On account of the large number of different sample shapes, the thermal contact between the sample and the crucible possibly has to be adapted for each individual sample. In this regard, there is relevant literature which deals with various possibilities for preparing samples (e.g. Achim Frick, Claudia Stern: DSC-Prüfung in der Anwendung. Munich and Vienna: Carl Hanser Verlag, 2006).

U.S. Pat. No. 7,470,057 and patent application DE 11 2007 001 888 disclose a sensor, wherein the support surfaces for the sample and the reference lie on the upper side of a sample platform and a reference platform. The sample platform and the reference platform are connected using diffusion welding to a cylindrical thin-walled element for the sample and to a cylindrical thin-walled element for the reference. The platforms for the sample and the reference are made of the one alloy of a thermocouple pair (alloy A) and the respectively associated cylindrical thin-walled elements are made of the other alloy of this thermocouple pair (alloy B). A base, which is made of the same alloy B as the cylindrical thin-walled elements, connects the latter together. A temperature difference can be measured via two wires made of alloy A, which are fixed to the undersides of the sample platform and the reference platform. It involves the difference between the mean temperature at the interface between the platform and the cylindrical thin-walled element on the reference side and the mean temperature at the interface between the platform and the cylindrical thin-walled element on the sample side. These interfaces lie outside the contact areas between the crucible and the platform. This is thus intended to ensure that the measured temperature differences remain independent of variations in the contact resistance, because the entire heat must flow via these interfaces according to the applicant's embodiments.

It is not taken into account here that, in the presence of a raised contact resistance between the crucible and the sensor, the heat flow proportions via radiation, heat conduction in the surrounding gas and convection increase in relative terms. The consequence of this is that the heat no longer flows to the same extent via the interface, which of course is at a certain distance from the crucible, and ultimately a smaller temperature difference, i.e. a weaker measurement signal, is built up.

In order that the thermal resistance is maintained and therefore the accuracy of the heat flow measurement is not impaired, the actual contact surfaces between the crucible base and the support surface must not vary for the various crucibles. The problem here, in particular, is that the crucible bases can deviate from an ideally flat shape in an uncontrolled and non-reproducible manner on account of the small material thickness. This may be caused by production, but also by deformation during handling. A curvature of the crucible base outwards becomes evident in a particularly disadvantageous manner for the reproducibility of the measurement results.

The problem underlying the invention, therefore, is to make available a method and a device for thermal material analysis and a sample holder with which the reproducibility of thermoanalytical measurements can be improved. Furthermore, it is a problem of the invention to provide a particularly effective production method for a holding device of a thermal analysis device.

SUMMARY OF THE INVENTION

According to the invention, the problem is solved by the fact that the support surface of a holding device and/or a sample holder comprise elevations or depressions forming contact points, which define a relevant heat flow zone assigned to the support surface, wherein a temperature detection region of the temperature detection means is disposed inside the relevant heat flow zone.

The invention proceeds from the consideration that, by means of a suitably selected embodiment of the sample holder and/or shape of the support surface, a thermal resistance between sample holder and sensor relevant to the measurement result and the reproducibility can for the most part be kept constant from measurement to measurement even with tolerance differences between the sample holders. The manufacturing precision of the sample holders can thus be comparatively low with identical or improved measurement accuracy, as a result of which the production costs for example can be reduced. The sample holder and the temperature measuring devices of the sensor could be constituted such that, without special measures being taken by the user, the thermal resistance between the crucible and the temperature detection means is largely the same from measurement to measurement. With otherwise identical boundary conditions such as temperature control and gas atmosphere, it could be assumed that the proportion that is attributable to the heat flow, the convection and the radiation does not change.

The elevations or depressions are located on the contact side at defined points of the sample holder and/or the holding device, as a result of which the heat conduction essentially takes place only via the contact point between the sample holder and the support surface. Contact points within the meaning of the invention are to be understood both as punctiform contact points as well as two-dimensionally extending contact points. The region between the contact points and the temperature detection means is referred to as the relevant heat flow zone. The arrangement of the temperature detection means and the sample holder takes place in such a way that the relevant heat flow zone remains constant from measurement to measurement due to the fact that the temperature detection means is disposed inside the relevant heat flow zone. The effect of this is that the heat flow determined by the temperature detection means remains largely constant on average in a plurality of measurement procedures.

The temperature detection means preferably comprises a contact shape corresponding to the elevations or depressions. Furthermore, it may be advantageous for the temperature detection region to run essentially centrally with respect to the support surface. The reproducibility can thus be further improved, since the heat conduction paths from the contact points to the temperature detection region thus diverge only negligibly from one another.

The contact points formed by the elevations or depressions preferably lie in an edge region of the support surface, which contributes to a stable arrangement of the sample holder on the support surface.

Depending on the application and its particular requirements, sample holders with different shapes and made of different materials are used for the measurements. The sample holder is particularly preferably constituted as a crucible. The mass of the crucible should be as small as possible, the heat conduction should be good and, for industrial use, the price should be as low as possible. It is proposed that use preferably be made of a crucible made of aluminium. The wall and base thicknesses of the crucible usually lie in the range of a few tenths of a millimeter, the filling volume between a few tens and a few hundred microliters. In the case of conventional crucibles for thermal analysis, the crucible bases diverge from one another for production-related reasons and on account of deformations due to mechanical effects, such as can occur during transport and handling. Without the contact points defined according to the invention, these deviations lead to a not insignificant measurement error.

It has proved to be particularly advantageous if a hollow space is constituted between the crucible base and the support surface. This can be achieved for example by the fact that the crucible base and/or the support surface comprises a depression in the form of a curvature. Through a differing shape of the curvature, it is thus possible to form, in cross-section, hollow spaces in the shape of a convex or concave lens, but also hollow spaces in meniscus form. The crucible base and/or the support surface preferably comprises a hollow space constituted in cross-section in the shape of a bi- or plano-convex lens. A curvature with a sinusoidal cross-section is however particularly preferred.

The temperature detection means is preferably integrated into the holding device. The temperature detection means can be a sensor, which is integrated into the holding device close to the support surface. The support surface itself is preferably constituted as a sensor. This can be achieved by the fact that the holding device is constituted as a thermocouple generating a measuring voltage, wherein an interface of two metal elements A, B forms the temperature measurement region. Depending on the embodiment, the temperature measurement region can have a different size and shape. For example, first metal element A can be surrounded by a second metal element B, as a result of which a closed contact shape arises and the temperature measurement region is defined taking account of the contact surface/interface.

A cylindrical holding device has proved to be particularly advantageous, wherein a first metal element A has a circular cross-section and is encased by a second cylindrical metal element B. The two metal elements form together a thermocouple, wherein the temperature measurement region runs in a circular manner. Such a holding device is regarded as being simple and cost-effective to produce compared to other embodiments. Especially with a crucible as the sample holder, the temperature measurement region thus has an advantageous profile corresponding to the sample holder.

The crucible for the device according to the invention preferably comprises a crucible base with a curvature directed towards the crucible. The hollow space thus formed between the crucible base and the support surface of the holding device thus has a plano-convex shape in cross-section, with a flat support surface. The edge of the curvature preferably terminates approximately with the outer edge of the crucible base, as a result of which a circumferential edge arises, which forms a kind of stand for the crucible and thus also for the contact surface according to the invention. It is thus also ensured at the same time that the crucible sits in a stable and secure manner on the support surface of the holding device. It is however also conceivable for the crucible to comprise punctiform elevations, three such elevations being regarded as sufficient for a stable stand.

A plurality of elevations or depressions should in principle be dimensioned uniformly and preferably be disposed homogeneously over the crucible base and/or the support surface.

With the use of the thermoanalytical measurement device according to the invention, a measurement method is for the first time enabled wherein the thermal resistance along the heat flow path between a sample and a reference remains for the most part identical in successive measurements due to the fact that the heat flow to be detected is conveyed to the temperature detection means essentially via defined contact points between the support surface and the sample holder. It is regarded as advantageous that the thermal resistance between the sample and the reference does not change significantly particularly when the position of the sample in the crucible and the position of the crucible on the sample holder each diverge from an ideally central position to a certain extent, depending on the embodiment of the order of magnitude of several tenths of a millimeter.

The thermocouple preferably used as a temperature detection means for the device and method according to the invention comprises at least two elements made of different metals, wherein a first metallic element A, with a higher expansion coefficient compared to a second metallic element B, is introduced in a precisely fitting manner into second metallic element B constituted as a hollow profile and the two elements A, B are heated in a first operational step and then cooled again in a second operational step. The effect of this is that the two elements A, B are welded together under high pressure due to different expansion coefficients (diffusion welding). In the presence of heating, element A expands more than element B, as a result of which the two elements are connected inseparably to one another under the influence of heat and pressure. The heating temperature preferably lies close to the solidus temperature of the lower-melting element. The blank is cooled down after the welding process.

In a particularly expedient embodiment, element A can have a smaller length than element B or can be disposed offset from element B in respect of the longitudinal axis of elements A, B, in such a way that an elevation according to the invention is formed by projecting element B.

In a further process stage, material of first element A is partially removed, preferably by means of a milling tool, in such a way that the hollow profile closed at one end is produced. It has proved to be advantageous for the milling process to be carried out in such a way that a material projection from element A is retained at the end face on the inner side of the hollow profile, as a result of which a contact element is formed for the thermocouple. During the milling process, a small material part is preferably also removed from element B at the side walls to compensate for tolerances and to ensure that all the material from element A is covered by the milling tool in the radial direction of the blank. Furthermore, it may be advantageous also to remove material from the welding zone.

The material projection is preferably constituted pin-like and disposed centrally in the hollow profile. Reliable and effective contacting is thus enabled. In a further expedient embodiment, the hollow profile is produced from two cylindrical parts. This has the advantage that the circular cross-sectional area, which represents the support surface for the sample holder, on the one hand corresponds to the shape of the crucible base and on the other hand the temperature detection region has a circular shape corresponding to the crucible base.

The contact element advantageously prevents or reduces distortion of the thermocouple due to the heat input during the contacting process. However, in order nonetheless to correct any distortion that may have occurred, the surface of the thermocouple acting as the support surface for the sample holder can be milled flat in a final operational step. If, as in the embodiment already mentioned as advantageous, element A has a smaller length than element B or if element A is disposed offset from element B in respect of the longitudinal axis of elements A, B, so that an elevation according to the invention is formed by projecting element B, face milling is of importance only for the surface of element B acting as a support surface for the sample holder.

For an inventive elevation or depression for the support surface, however, a partial vacuum can for example also be generated in the finished hollow profile in order to achieve an inwardly directed curvature of the support surface through its plastic deformation. Instead of the generation of a partial vacuum, or in addition, an inventive shape of the support surface can also be achieved with a force acting inwards on the opposite side of the support surface.

The advantages obtained with the invention consist in particular in the fact that the holding device according to the invention at the same time serves as a sensor and can be produced comparatively easily and cost-effectively. Due to the elevations or depressions disposed in a defined manner on the support surface and/or crucible bases, a plurality of measuring procedures can be carried out using a plurality of crucibles without time-consuming recalibration. The crucible and the temperature measuring device are constituted such that, without the user taking additional measures, the thermal resistance between the crucible and the temperature detection means is for the most part the same from measurement to measurement. The device according to the invention can be used, amongst other things, both for a power-compensating DSC as well as for a heat flow DSC. Furthermore, the device according to the invention is suitable for all thermal analysis methods with one or more crucibles.

BRIEF DESCRIPTION OF THE DRAWINGS

Examples of embodiment of the invention are described by way of example by reference to the appended drawings.

In the figures.

DETAILED DESCRIPTION OF THE INVENTION

Identical elements are provided with the same reference numbers in all the figures.

Figure 1:
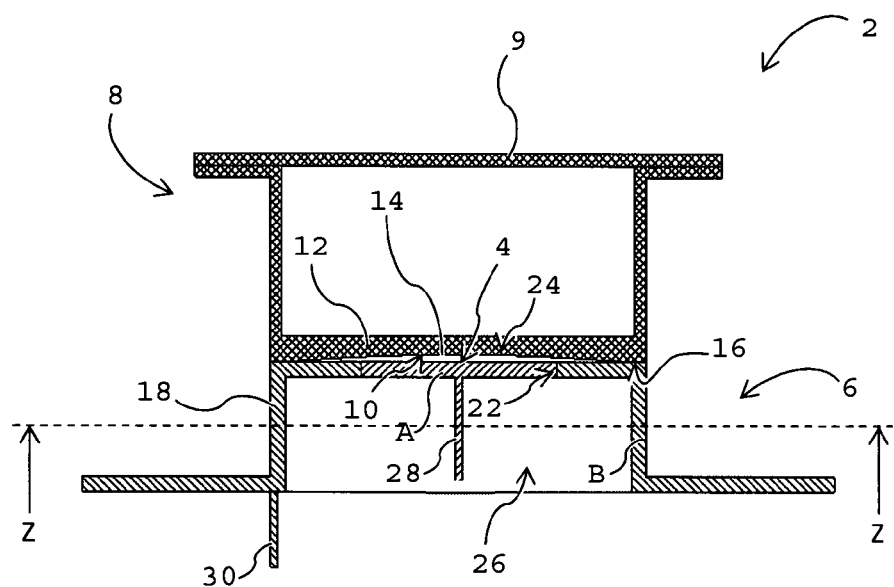
FIG. 1 shows diagrammatically in cross-section a temperature measuring device with a plane support surface of the holding device and a crucible with a crucible base curved inwards.

FIG. 1 shows in cross-section a temperature measuring device 2 for dynamic differential calorimetry with a plane support surface 4 of holding device 6 and a metallic crucible 8 as a sample holder with a depression 10 in the form of an inwardly curved crucible base 12. Holding device 6 and crucible 8 for the sample and the reference side are identical. Support surface 4 of the sample side and the reference side are connected together thermally and electrically.

A hollow space 14 thus arises between crucible 8 and support surface 4, said hollow space having in cross-section the shape of a plano-convex lens, as result of which crucible 8 is seated only in an edge region and crucible base 12 is in contact with support surface 4 of holding device 6 via a contact surface 16 thus formed. Temperature detection means 18 is integrated in holding device 6, in such a way that holding device 6 is constituted as a thermocouple 18 in the region of support surface 4. An interface 22 of thermocouple 18 represents a temperature detection region, formed by a first and a second metallic element A, B, which are in contact with one another. This temperature detection region has no direct contact with crucible base 12, since crucible 8 is shaped in such a way that, on account of a curvature 24 in crucible base 12, the temperature detection region lies below this curvature 24. The influence of otherwise common production-related variations in the shape of crucible base 12 on the heat flow diminishes and the reproducibility increases.

Crucible 8 and holding device 6 have a circular cross-section. Crucible 8 is provided with a cover 9 before the start of the measurement. Cover 9 ensures a homogeneous temperature field. Holding device 6 was fashioned out of a cylindrical blank by means of a milling tool. For this purpose, a metallic element A constituted as a cylindrical solid profile is introduced in a precisely fitting manner at room temperature into a second metallic element B constituted as a cylindrical hollow profile. Element A has a higher expansion coefficient than element B. Nickel-chromium/constantan was used as the thermocouple pair element A/element B.

In a first operational step, the blank is heated to approx. 1200° C., as a result of which elements A, B are welded together under the influence of pressure and heat (diffusion welding). After the cooling of the blank, material is removed, essentially from element A, with the aid of a milling tool, the milling tool being moved in the axial direction with respect to the blank. The milling tool is dimensioned and adjusted such that, with an additional movement along a circular path around the longitudinal axis of the blank, a recess 26 is produced which corresponds to a sought wall thickness s of the holding device 6. A pin-like material projection 28 formed on the end face serves as a contact element. In order to compensate for manufacturing tolerances and to ensure that the material is removed completely from element A inside recess 26, material is also removed from element B in the radial direction. For this purpose, element B has, before the milling process, a wall thickness s' (not represented here) which is greater than wall thickness s of finished holding device 6.

Apart from contact element 28 produced by the milling process, element B is also provided with a contact element 30. During a contacting process, for example by resistance welding, heat is introduced into contact elements 28, 30 due to the process and is partially transmitted to holding device 6, which can lead to a distortion of holding device 6. In particular, the distortion of support surface 4 can occur. This undesired effect also cannot be eliminated as in this embodiment, by the fact that contact element 28 and support surface 4 formed by element A are constituted in one piece and the heated contact point is thus advantageously spaced apart from support surface 4. A distortion that has arisen can finally be corrected by face milling of the support surface 4.

In a measurement procedure taking the example of a heat flow DSC, a sample (not shown here) is positioned in crucible 8 and heated. The accuracy of the measurement of the heat flow is dependent on the reproducibility of the individual measurement. To this end, the total thermal resistance between the sample and the reference along the heat flow path should remain constant in successive measurements. According to the invention, and taking the example of the embodiment shown here, this is achieved by the fact that sample holder 8 comprises a depression in the form of a curvature 24 forming contact points 16, wherein contact points 16 define a relevant heat flow zone assigned to support surface 4. Located in the end region of this heat flow zone is the temperature detection region of holding device 6.

Crucible 8 sits in a stable manner on support surface 4 by means of the circumferential edge region formed by curvature 24 in crucible base 12. In theory, crucible base 12 is in contact with support surface 4 via the edge surface. However, crucible base 12 is in fact in contact with support surface 4 via a plurality of contact points 16, which are distributed over the entire edge surface, but which are located in a firmly defined region. This region limits the heat flow zone of support surface 4 to the exterior. The major part of the heat transfer between crucible 8 and support surface 4 takes place however in this region. The height of hollow space 14 between crucible base 12 and support surface 4 can vary within small manufacturing tolerances. With this example of embodiment, it is only important for the invention that a hollow space 14 is present and surface 16 of the contacting region does not change despite a differing curvature 24.

Hollow space 14 between crucible base 12 and support surface 4 is at most only a few hundredths of a millimeter high at its highest point in the vicinity of the centre-point of the circular support surface. The heat exchange through hollow space 14 therefore takes place essentially by heat conduction through the gas that is present in hollow space 14. On account of the small height of hollow space 14, convection plays only a subordinate role. It is also advantageous that the gas molecules are enclosed in hollow space 14 and the heat losses to the external region, which are then also possible through convection, are thus minimised. Hollow space 14 can also be regarded as a nominally closed-off hollow space 14, and not as an actually closed-off hollow space, since an at least small gas exchange between hollow space 14 and the atmosphere can be assumed due to the roughness of the surfaces involved. In order to prevent, in an exceptional case, the occurrence in hollow space 14 of an abrupt pressure drop during heating and the creation of a partial vacuum during cooling, grooves (not represented here) with a small depth of a few hundredths of a millimeter can for example be introduced into support surface 4 or crucible base 12, through which grooves a pressure compensation can then take place. A further possibility would be to provide crucible base 12, instead of continuous circular contact surface 16, with punctiform elevations along the circular line.

Figure 2:
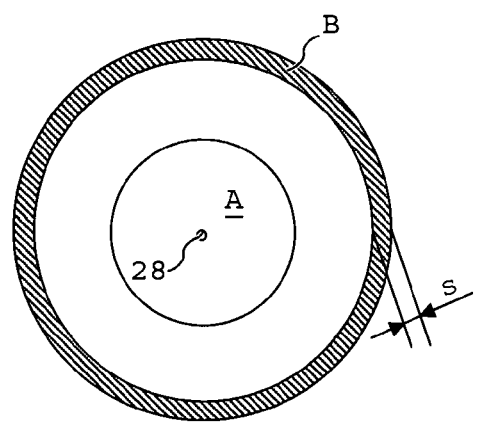
FIG. 2 shows diagrammatically a cross-section of the temperature measuring device.

FIG. 2 shows a cross-section Z-Z through holding device 6 represented in FIG. 1. Jacket-shaped wall thickness s corresponds to the wall thickness after the milling process, which is smaller than an original wall thickness s' of the blank. The two metallic elements A, B forming thermocouple 18 are connected together by diffusion welding, wherein the contact line together with the wall thickness of support surface 4 define the temperature detection region. Disposed centrally at the underside of support surface 4 is contact element 28.

Figure 3:
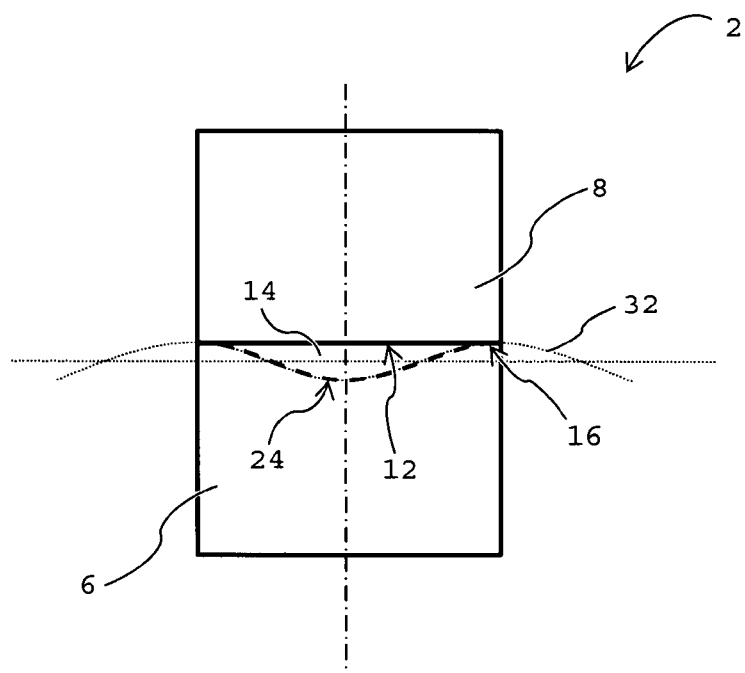
FIG. 3 shows diagrammatically a crucible-sensor arrangement and a support surface comprising a depression with an inward curvature running sinusoidally in cross-section.

An arrangement with a holding device 6 and a crucible 8, represented diagrammatically in a very simplified form, is shown in FIG. 3. Here, by way of example, support surface 4 of holding device 6 is curved inwards and has a sinusoidal course 32. Hollow space 14 between support surface 4 and crucible base 12 corresponds approximately to the shape of a plano-convex lens. Approximately means that the profiles of the contact surfaces can be not only arcs of a cycle, but also approximated by polynomials of any order or trigonometric functions such as simply sines or cosines.

Figure 4A:
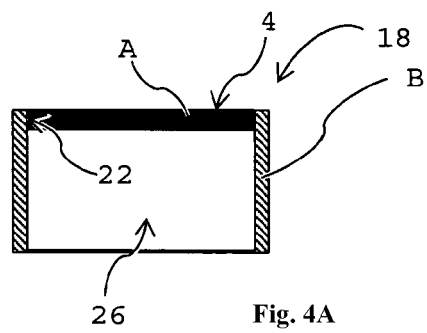
FIGS. 4A-4C shows diagrammatically various examples of embodiment of a thermocouple.
Figures 4B, 4C:
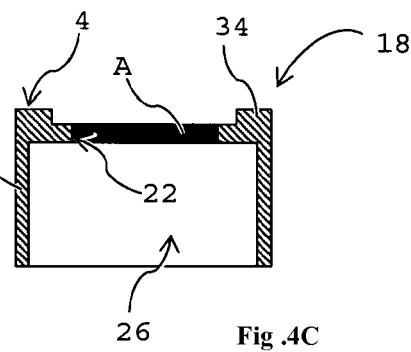

FIGS. 4A to 4C show in cross-section various embodiments of a holding device 6. The embodiments denoted by FIGS. 4A and 4B comprise a flat support surface 4, so that, in order to arrive at the device according to the invention, crucible base 12 has to be provided with elevations or depressions 10 forming contact points 16. A drawback with embodiment 4B compared to 4A is the temperature detection region of thermocouple 18 constituted beneath the carrier plate acting as a support surface 4. Such a structure can have an unfavourable effect on the measurement result.

Holding device 6 shown under 4C represents a holding device 6 modified with respect to embodiment 4A. Support surface 4 is provided in an edge region with an elevation 34 forming contact points 16, said elevation having a closed shape running around support surface 4.

Figure 5:
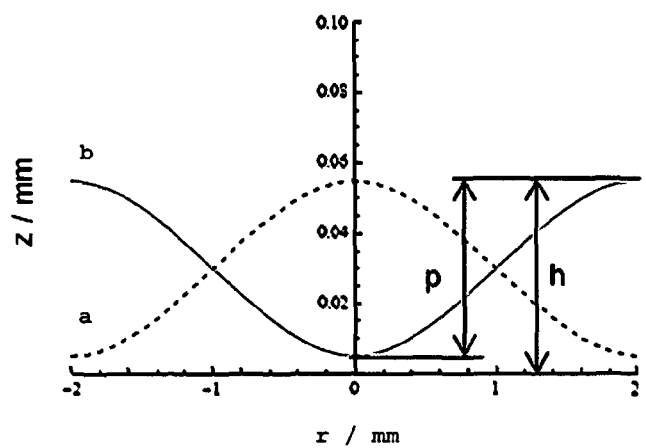
FIG. 5 shows diagrammatically profiles of the crucible base.

In FIG. 5, curve a shows the profile of crucible base 12, wherein z represents the distance of crucible base 12 from the support surface 4 as a function of r, the distance to the centre-point of support surface 4. The radius of crucible base 12 amounts to 2 mm. Profile b, on the other hand, shows a crucible base 12, which makes contact with support surface 4 of thermocouple 18 in a pointwise manner in the centre of support surface 4. The profile height is denoted by p and the maximum distance between crucible base 12 and support surface 4 is denoted by h in the illustration, said distance lying in the region of a few hundredths of a millimeter. Both curves a, b show a minimum value of 5 µm (mean roughness). It is thus taken into account for the calculation of the contact resistance between the support surface and crucible 8 carried out with represented profiles a and b that a certain roughness exists for the contacting surfaces.

Figure 6:
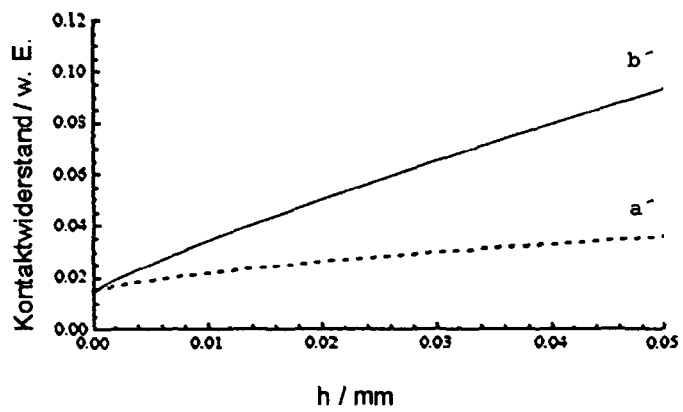
FIG. 6 shows diagrammatically the result of the calculation of contact resistance as a function of maximum distance h for the profiles in FIG. 5.

FIG. 6 shows, with curve a', the result of the calculation of the contact resistance, produced through the entire gas layer, between support surface 4 and crucible 8 as a function of maximum distance h for profile a plotted in FIG. 5. As shown in the representation, the contact resistance scarcely varies with maximum distance h.

In contrast with this, a marked dependence of the contact resistance on h can be seen in the case of curve b'. Curve b' was calculated on the basis of profile b in FIG. 5. The maximum distance here lies in the region of a few hundredths of a millimeter with p=h-5 µm. In the case of described curvature 24, the thermal resistance is admittedly slightly higher than in the case of an ideally flat crucible base, but the reduction in the measurement signal associated with curvature 24, which lies in a comparatively very small percentage range, is negligible compared to the improvement in the reproducibility.

The method, device and sample holder are specifically orientated towards an improved reproducibility of measurement results, with which the influence of deviations in the shape of crucible base 12 on the heat flow is markedly reduced. This is achieved by elevations 34 and/or depressions 10 in the contact region between crucible base 12 and support surface 4 of holding device 6, which are located at specific points inside the contact region.

The invention claimed is:

1. A thermal analysis device comprising:
a holding device with a support surface for a sample holder, the support surface having at least one temperature detector, characterized in that the support surface and/or the sample holder comprise elevations or depressions forming contact points, which define a relevant heat flow zone assigned to the support surface, and wherein a temperature detection region of the temperature detector is disposed inside the relevant heat flow zone.

2. The thermal analysis device according to claim 1, characterized in that the temperature detector has a contact shape corresponding to the elevations or depressions.

3. The thermal analysis device according to claim 1, characterized in that the temperature detection region runs centrally with respect to the support surface.

4. The thermal analysis device according to claim 1, characterized in that the contact points lie in an edge region of the support surface.

5. The thermal analysis device according to claim 1, characterized in that the temperature detector is integrated into the holding device.

6. The thermal analysis device according to claim 1, characterized in that the temperature detector is a thermocouple.

7. The thermal analysis device according to claim 6, characterized in that the thermocouple comprises a first metal and a second metal surrounding the first metal, wherein the first and second metals form the support surface for the crucible.

8. The thermal analysis device according to claim 7, characterized in that the temperature detection region is constituted by an interface of the first and second metals.

9. The thermal analysis device according to claim 1, characterized in that the sample holder is a crucible.

10. The thermal analysis device according to claim 9, characterized in that a hollow space is provided between a base of the crucible and the support surface.

11. The thermal analysis device according to claim 10, characterized in that the hollow space is formed in a curvature of the crucible base and/or the support surface.

12. The thermal analysis device according to claim 11, characterized in that the hollow space corresponds in cross-section approximately to a shape of a convex lens.

13. The thermal analysis device according to claim 11, characterized in that the hollow space corresponds in cross-section approximately to a shape of a concave lens.

14. A thermoanalytical measurement method comprising:
using a thermal analysis device having a holding device with a support surface for a sample holder, the support surface having at least one temperature detector, characterized in that a heat flow to be detected is conveyed to the temperature detector via contact points disposed in a defined manner between the support surface and the sample holder.

15. The thermoanalytical measurement method according to claim 14, characterized in that the heat flow detection takes place beneath a hollow space provided by the support surface of the holding device and/or the sample holder.

16. A thermal analysis device comprising:
a holding device with a support surface for a sample holder, the support surface having at least one temperature detector, the temperature detector including at least two elements made of different metals, wherein a first metallic element, with a higher expansion coefficient compared to a second metallic element, is introduced in a precisely fitting manner into the second metallic element having a hollow profile, and the first and second metallic elements are heated in a first operational step and then cooled again in a second operational step,
wherein the support surface and/or the sample holder comprise elevations or depressions forming contact points, which define a relevant heat flow zone assigned to the support surface, and
wherein a temperature detection region of the temperature detector is disposed inside the relevant heat flow zone.

* * * * *